US00PP13270P3

(12) United States Plant Patent

Olesen et al.

(10) Patent No.: US PP13,270 P3

(45) Date of Patent: Nov. 26, 2002

(54) SHRUB ROSE VARIETY 'POULATTRA'

(76) Inventors: L. Pernille Olesen, Hillerødvejen 49, DK-3480, Fredensborg (DK); Mogens N. Olesen, Hillerødvejen 49, DK-3480, Fredensborg (DK)

( * ) Notice: Subject to any disclaimer, the term of this patent is extended or adjusted under 35 U.S.C. 154(b) by 0 days.

(21) Appl. No.: 09/776,563

(22) Filed: Feb. 1, 2001

(65) Prior Publication Data

US 2002/0152507 P1 Oct. 17, 2002

(51) Int. Cl.[7] ..... A01H 5/00

(52) U.S. Cl. ..... Plt./108

(58) Field of Search ..... Plt./108

*Primary Examiner*—Bruce R. Campell
*Assistant Examiner*—A. Para

(57) ABSTRACT

A new shrub rose which has abundant, dark red flowers and attractive foliage. This new and distinct variety has shown to be uniform and stable in the resulting generations from asexual propagation.

1 Drawing Sheet

CLASSIFICATION

Botanical: *Rosa hybrida* 'POULattra'.

Commercial: Shrub rose.

SUMMARY OF THE INVENTION

The present invention constitutes a new and distinct variety of shrub rose which originated from a controlled crossing between 'Kormixal Suffolk' and 'an unnamed seedling', both unpatented varieties. The two parents were crossed during the summer of 1993 and the resulting seeds were planted in a controlled environment in Fredensborg, Denmark. The new variety is named 'POULattra'.

The new rose may be distinguished from its seed parent, 'Kormixal Suffolk', by the following combination of characteristics:

1. 'POULattra' exhibits dark red blooms, whereas 'Kormixal Suffolk' exhibits lighter red blooms with a yellow center.

2. 'POULattra' has small double blooms, whereas the seed parent has semi-double blooms.

The new variety may be distinguished from its pollen parent, 'an unnamed seedling' by the following combination of characteristics:

1. 'POULattra' is a shrub rose with a spreading, bushy habit, whereas the pollen parent is a miniature rose.

2. 'POULattra' has larger leaves and more foliage than the pollen parent.

The objective of the hybridization of this rose variety was to create a new and distinct variety for garden use with unique qualities, such as:

1. Uniform and abundant dark red flowers;

2. Vigorous, but compact growth when propagated both as a budded rose and on its own roots;

3. Disease resistance.

This combination of qualities is not present in previously available commercial cultivars of this type and distinguish 'POULattra' from all other varieties of which we are aware.

As part of their rose development program, L. Pernille Olesen and Mogens N. Olesen germinated the seeds from the aforementioned hybridization during winter 1993 and conducted evaluations on the resulting seedlings in a controlled environment in Fredensborg, Denmark.

'POULattra' was selected in the spring 1994 by the inventors as a single plant from the progeny of the aforementioned hybridization. Asexual reproduction of 'POULattra' by traditional budding and rooted cuttings was first done by L. Pernille and Mogens N. Olesen in their nursery in Fredensborg, Denmark in summer 1994. This initial and other subsequent asexual propagations conducted in controlled environments have demonstrated that the characteristics of 'POULattra' are true to type and are transmitted from one generation to the next.

BRIEF DESCRIPTION OF THE DRAWING

The accompanying color illustration shows as true as is reasonably possible to obtain in color photographs of this type the variety rose 'POULattra'. Specifically illustrated in SHEET 1 are 'POULattra's' foliage, flower buds, partially open buds, and open blooms.

DETAILED DESCRIPTION OF THE VARIETY

The following is a description of 'POULattra', as observed in its growth in a nursery in Jackson County, Oreg., on plants aged 1 one year. Color references are made using The Royal Horticultural Society (London, England) Colour Chart, 1995, except where common terms of color are used.

For a comparison, several physical characteristics of the rose variety 'POULria', a rose variety from the same inventors described and illustrated in U.S. Plant patent application Ser. No. 09/274,686 dated Mar. 24, 1999 are compared to 'POULattra' in Chart 1.

CHART 1

| | 'POULattra' | 'POULria' |
|---|---|---|
| Color of open flower, outer side, middle zone. | Red Group 53D | Red Group 53A to Red-Purple Group 59C. |
| Petalage | 20–25 | 40–50 |
| Upon opening, color basal petal spot, outer side | Yellow Group 4D | White Group 155C |

Classification:
*Botanical.*—*Rosa hybrida* 'POULattra'.
*Commercial.*—Shrub rose.
Parents:
*Seed parent.*—'Kormixal Suffolk'.
*Pollen parent.*—'Unnamed seedling'.

FLOWER AND FLOWER BUD

Blooming habit: Continuous.
Flower bud:
*Bud form.*—Ovate.
*Sepals.*—Size: 15 mm long and 10 mm wide. Appendages: Weak appendages. Texture: Moderately pubescent. Color: Upper surface is Yellow-Green Group 144A. Lower surface is Yellow-Green Group 144B and Red-Purple Group 59B.
*Receptacle.*—Size: 10 mm (l)×10 mm (w).
*Peduncle.*—Surface: Many fragrant stipitate glands present. Color: Yellow-Green Group 144B, with anthocyanin intonations of Red-Purple Group 71B. Strength: Strong. Length: 20 to 22 cm.
*Borne.*—From top of plant. Between 5 to 40 flowers per branch.
Flower bloom:
*Fragrance.*—Slight spicy scent.
*Size.*—Small. Average flower diameter is 40–60 mm when open.
*Form.*—Shape of flower when viewed from the side: Upper part: Flat. Lower part: Flat. Viewed from above: Irregularly rounded.
*Petalage.*—Double. Average range: 20–25 petals under normal conditions.
Color:
*Petals.*—Inner Side: Middle zone: Red Group 53A. Marginal zone: Red Group 53A. Basal petal spot: Yellow Group 4D. Outer side: Middle zone: Red Group 53D. Marginal zone: Red Group 53D. Basal petal spot: Yellow Group 4D.
*General tonality.*—On open flower Red Group 53D. No change in the general tonality.
Petals:
*Petal reflex.*—Slight.
*Petal edge.*—Entire.
*Size.*—25 mm (l)×20 mm (w).
*Shape.*—Obovate. Petal apex is rounded. Petal base is acute.
*Surface texture.*—Velvety.
*Duration.*—8 to 10 days.
*Persistence.*—Petals fall cleanly from the stem.
*Arrangement.*—Formal.
*Petaloids.*—Quantity: 4 to 6. Size: 10 mm (l)×7 mm (w). Color: Red Group 53A. Surface Texture: Velvety.
Reproductive organs:
*Anthers.*—Size: 1 to 2 mm long. Quantity: 15 to 20. Color: Yellow Group 13A.
*Filaments.*—Color: Yellow Group 2B.
*Stigmas.*—Position: Slightly superior to anthers. Color: Yellow-Green Group 150C.
*Pistils.*—Size: 7 to 8 mm long. Quantity: 10 to 14.
*Styles.*—Color: Greyed-Yellow Group 160D.
*Hips.*—None observed.
*Pollen.*—Color: Yellow Group 17A. Quantity: Scant.

PLANT

Plant growth: Low, compact, bushy to slightly spreading, even growth. When grown as a budded field grown plant on *Rosa multiflora* understock, the average height of the plant is 40–60 cm and the average width is 50 cm.
Stems:
*Thorns.*—Incidence: 12 to 15 per 10 cm of stem. Size: 6 mm. Shape: Deeply concave. Color: Greyed-Yellow Group 160C.
*Color.*—Young wood: Yellow-Green Group 144B. OIder wood: Yellow-Green Group 144B.
*Texture.*—Young wood: Smooth. Older wood: Smooth.
Plant foliage:
*Leaf size.*—62 mm (l)×33 mm (w).
*Abundance.*—Average.
*Glossy.*—Upper side average glossiness.
*Color, mature foliage.*—Upper Leaf Surface: Green Group 137A. Lower Leaf Surface: Green Group 137D.
*Color, juvenile foliage.*—Upper Leaf Surface: Green Group 137B. Lower Leaf Surface: Green Group 137D.
*Anthocyanin intonation.*—Color: Red-Purple Group 61A.
Plant leaves and leaflets:
*Stipules.*—Size: 12 mm long. Color: Yellow Green 144A. Stipitate Glands: Present on stipule margins. Anthocyanin: Red-Purple Group 61A.
*Petiole.*—Length: 5 to 7 mm (l). Color: Yellow-Green Group 144A. Underside: Yellow-Green Group 144A.
*Rachis.*—Length: 5 to 7 mm (l). Color: Yellow-Green Group 144A. Underside: Yellow-Green Group 144A.
*Leaflet.*—Cross Section: Slightly concave. Margin Type: Serrated. Shape: Ovate. Apex is acute, base is rounded.
*Terminal leaflet.*—Length of blade: 15 to 20 mm. Width of blade: 10 to 12 mm. Shape: Ovate.
Disease resistance: Above average resistance to mildew, rust, black spot, and Botrytis under normal growing conditions in Fredensborg, Denmark and Hannover, Germany.
Cold hardiness: The variety 'POULattra' has been found to be cold hardy in Fredensborg, Denmark and Hannover, Germany.
We claim:
1. A new and distinct variety of rose plant of the shrub rose class, substantially as herein illustrated and described as a distinct and novel rose variety due to its abundant dark red flowers, disease resistance, and extended period of bloom.

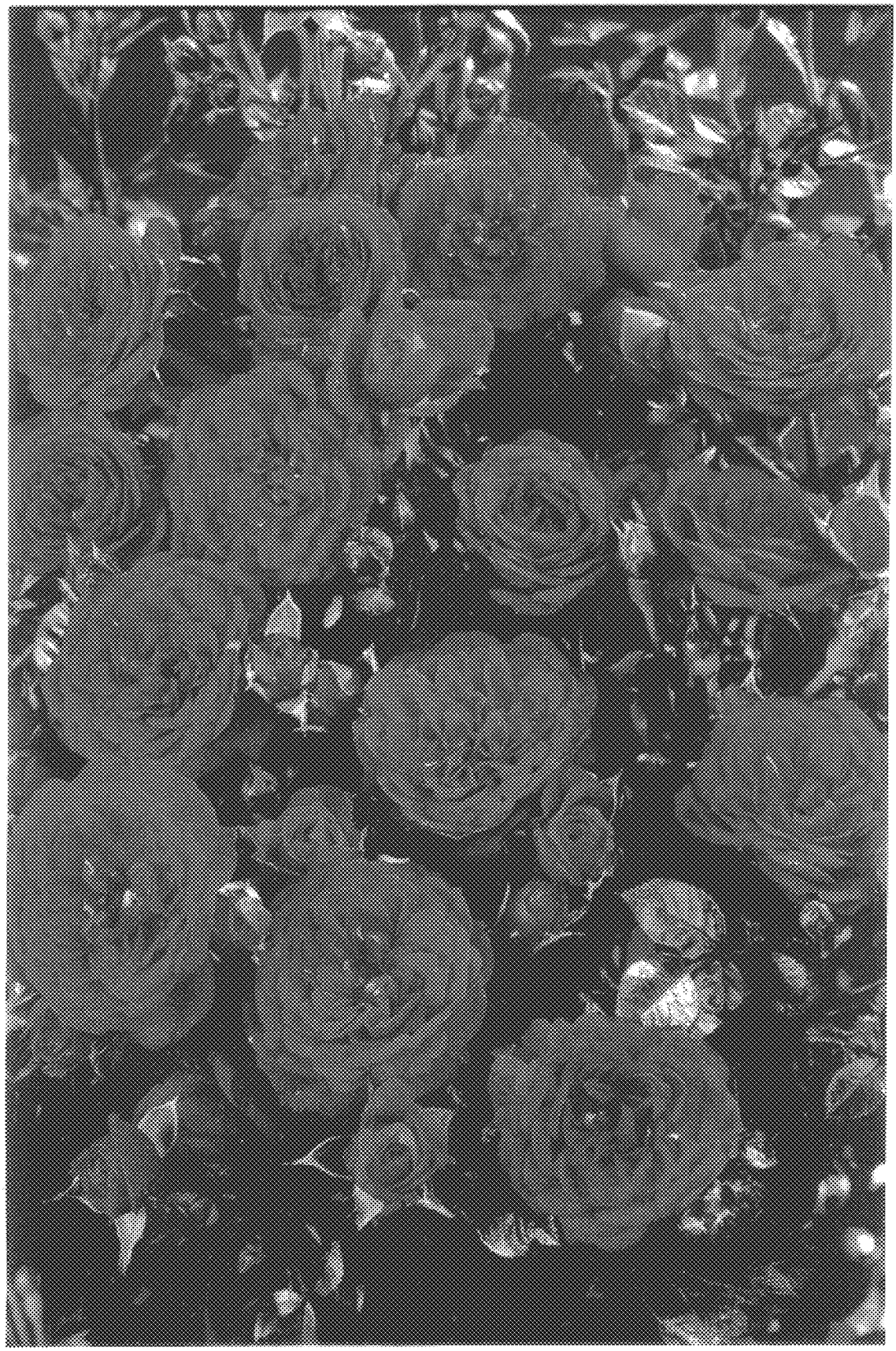

* * * * *